(12) United States Patent
Beck-Nielsen

(10) Patent No.: US 8,118,741 B2
(45) Date of Patent: Feb. 21, 2012

(54) METHOD AND APPARATUS FOR PREDICTION AND WARNING OF HYPOGLYCAEMIC ATTACK

(75) Inventor: Henning Beck-Nielsen, Odense M (DK)

(73) Assignee: Hypo-Safe A/X, Odense (DK)

( * ) Notice: Subject to any disclaimer, the term of this patent is extended or adjusted under 35 U.S.C. 154(b) by 461 days.

(21) Appl. No.: 11/793,271

(22) PCT Filed: Nov. 21, 2005

(86) PCT No.: PCT/DK2005/000739
§ 371 (c)(1),
(2), (4) Date: Feb. 19, 2008

(87) PCT Pub. No.: WO2006/066577
PCT Pub. Date: Jun. 29, 2006

(65) Prior Publication Data
US 2009/0062678 A1   Mar. 5, 2009

(30) Foreign Application Priority Data
Dec. 20, 2004   (DK) .................................. 2004 01955

(51) Int. Cl.
*A61B 5/00* (2006.01)

(52) U.S. Cl. ......... 600/365; 600/347; 600/544; 600/545

(58) Field of Classification Search ................. 600/347, 600/365, 544, 545
See application file for complete search history.

(56) References Cited

U.S. PATENT DOCUMENTS

| | | |
|---|---|---|
| 4,295,474 A | 10/1981 | Fischell |
| 6,354,299 B1 | 3/2002 | Fischell et al. |
| 6,360,122 B1 | 3/2002 | Fischell et al. |
| 6,572,542 B1 | 6/2003 | Houben et al. |
| 6,583,796 B2 | 6/2003 | Jamar et al. |
| 7,029,443 B2 | 4/2006 | Kroll |
| 7,136,703 B1 | 11/2006 | Cappa et al. |

(Continued)

FOREIGN PATENT DOCUMENTS

| | | |
|---|---|---|
| DE | 10248894 A1 | 5/2004 |
| EP | 1419731 A1 | 5/2004 |
| WO | 2005037092 A1 | 4/2005 |

OTHER PUBLICATIONS

Stig Pramming et al, "Glycaemic threshold for changes in electroencephalograms during hypoglaecemia in patients with insulin dependent diabetes," British Medical Journal, vol. 206, Mar. 5, 1998, pp. 665-667.*

(Continued)

*Primary Examiner* — Miranda Le
*Assistant Examiner* — Karen Toth
(74) *Attorney, Agent, or Firm* — Sughrue Mion, PLLC

(57) ABSTRACT

The present invention includes a method and device for warning of hypoglycaemic attacks, which is a big problem for especially diabetics, who are in insulin treatment. It is estimated that about 1 million people have a decreased quality of life as a result of hypoglycaemic attacks. The invention collects EEG signals from people, who must be supervised and analyses these in order to detect characteristic changes in the EEG signals, which occurs in advance of a hypoglycaemic attack. In a preferred embodiment the EEG signals are collected with subcutaneously placed electrodes and the signals are lead via wires drawn under the person's skin to a similar subcutaneously placed signal processing unit. The signal processing analyses the EEG signals and when the pre-seizure characteristics signal changes are detected, a warning signal is given to the person from an alarm giver build into the signal processing unit, e.g. in form of a vibrator. When a person detects a warning signal, the person can prevent the hypoglycaemic attack by e.g. consuming a sugary food.

10 Claims, 5 Drawing Sheets

U.S. PATENT DOCUMENTS

| | | | |
|---|---|---|---|
| 7,299,085 | B2 | 11/2007 | Bergelson et al. |
| 7,299,086 | B2 | 11/2007 | McCabe et al. |
| 2002/0099412 | A1 | 7/2002 | Fischell et al. |
| 2006/0049957 | A1* | 3/2006 | Surgenor et al. ......... 340/825.19 |
| 2008/0183097 | A1 | 7/2008 | Leyde et al. |
| 2008/0234598 | A1 | 9/2008 | Snyder et al. |

OTHER PUBLICATIONS

G Tribl et al, "EEG topography during insulin-induced hypoglycemia," European Neurology, 1996, 36(5) pp. 303-309.*

Bendtson, I., et al., "*Nocturnal Electrocephalogram Registration in Type I Insulin-Dependent Diabetic Patients with Hypoglycaemia,*" Diabetologia 1991, vol. 34, nr. 10, pp. 750-756, ISSN 0012-186X.

Bjorgaas, M. et al., "*Quantitative EEG During Controlled Hypoglycaemia in Diabetic and Non-Diebetic Children,*" Diabetic Medicine 1998, vol. 15, nr. 1, pp. 30-37, ISSN 0742-3071 (Print).

Heger, G. et al., "*Monitoring Set-Up for Selection of Parameters for Detection of Hypoglycaemia in Diabetic Patients,*" Medical & Biological Engineering & Computing 1996, vol. 34, pp. 69-75.

Howorka, K. et al., "*Severe Hypoglycaemia Unawareness is Associated With an Early Increase in Vigilance During Hypoglycaemia,*".

Tupola, S. et al., "*Abnormal Electroencephalogram at Diagnosis of Insulin-Dependent Diabetes Mellitus May Predict Severe Symptoms of Hypoglycemia in Children,*" Journal of Pediatrics, Dec. 1998, vol. 133, nr. 6, pp. 792-794, ISSN 0022-3476.

Published PCT International Search Report; PCT/DK2005/000739, dated Apr. 11, 2006.

Supplementary European Search Report for EP05803996 dated Oct. 4, 2011.

F. Iaione et al, "Methodology for hypoglycaemia detection based on the processing, analysis and classification of the electroencephalogram", Medical & Biological Engineering & Computing, vol. 43, No. 4, Jul. 1, 2005, pp. 501-507 XP001508909.

J. Gade et al, Detection of EEG Patterns Related to Nocturnal Hypoglycemia, Methods of Information in Medicine, vol. 33, No. 1, Mar. 1994, pp. 153-156 XP000002659531.

\* cited by examiner

METHOD AND APPARATUS FOR PREDICTION AND WARNING OF HYPOGLYCAEMIC ATTACK

The invention relates to a method of predicting and warning of hypoglycaemic attacks for people such as diabetics.

Moreover the invention relates a device for prediction and warning of hypoglycaemic attacks for people such as diabetics.

Hypoglycaemic attacks occur as a result of a too low blood sugar concentration, which is mostly a problem for diabetics, who are treated with insulin or other blood sugar regulating medical drugs.

The attacks can be highly severe and often entail unconsciousness.

The risk of an attack therefore often limits the possible activities of the people, which furthermore decreases the quality of life for these people.

Attacks can in a simple way be prevented if the people e.g. consume appropriate food when the glucose values become critical.

The problem is however that many in the risk group cannot by themselves feel when the blood sugar concentration reaches a critically low level with risk of an attack.

The number of people in the risk group is approximately 1 million.

There are known methods and devices for prediction of hypoglycaemic attacks.

In U.S. Pat. No. 6,572,542 a method and a device are described, which among others have the purpose of warning hypoglycaemic attacks.

The known technique primarily uses registration of changes in a person's ECG (electrocardiographic) signals as a result of a critically low level of blood sugar, to emit a signal of warning. The changes in the ECG signals are in an example described in the patent specification linked with EEG (electroencephalographic) signals from the person in order to clarify the blood sugar dependent changes in the ECG signal.

It has been found, however, that this prior art involves some drawbacks.

Since the technique requires signal analysis of both the ECG and EEG signals from the person, who is being measured on, the algorithms for calculating become relatively complex, which specifies high demands for hardware processing power and at the same time demands a high power draw.

If this is linked together with the fact that a relatively high number of electrodes for both ECG and EEG signal collection are necessary, it results in a relatively big and complex product, which is difficult to apply in the daily life of a person.

It is furthermore generally known that the greater complexity a product contains, the greater is the risk that the product will become unstable.

The mentioned drawbacks have overall meant that the hitherto known technique has not resulted in the manufacturing of products, which can enhance the quality of life for wide parts of the risk group.

It is therefore a purpose of the invention to improve the known method and the known device.

The object of the invention is achieved by a method of the type stated in the introductory portion of claim 1, which is characterized in that the warning is based on analysis of one or more EEG signals from the person.

Hereby, it is thus possible to reduce the number of electrodes, since the ECG signal is not going to be used, simultaneously the complexity is reduced, and the demands for processing power and the need for power draw is also reduced.

In this way it is possible to manufacture a simple, robust and highly portable alarm system, which basically everyone in the seizure risk group can have advantage of.

As stated in claim 2 it is furthermore a special feature of the invention that the warning is given after signal analytic identification of pre-seizure characteristic EEG changes such as decrease in frequency and increase in amplitude.

Tests have shown that the EEG signal changes in a simple and characteristic way in the time leading to a hypoglycaemic attack. A signal analytic identification of the characteristic changes in the frequency and amplitude has shown to be a good, safe and robust basis for release of an alarm signal.

The alarm signal can be released in sufficient time before a seizure is triggered, so that the person can easily have time to prevent an attack.

In claim 3 is stated that it is furthermore a special characteristic of the invention that the EEG signals are registered from two or more electrodes placed intracranially or extracranially on the skin surface or subcutaneously.

By placing the EEG electrodes outside the skin the electrode to skin contact impedance and thus the signal detection will vary with e.g. the moisture of the skin and the head movement of the patient. If the electrodes are placed subcutaneous the location will be permanent and the electro impedance more stable, which makes the whole warning system more robust.

It is stated in claim 4 that it is furthermore a characteristic of the invention that the EEG signals from the electrodes are transmitted via subcutaneously drawn wires to a subcutaneous placed signal interface unit or signal processing—and alarm unit.

With these characteristics it is among other made possible to manufacture a warning system for hypoglycaemic attacks, which is not visible, since the whole unit can be placed subcutaneously.

Further preferred embodiments of the method of the invention are defined in claims 5 through 8.

As mentioned the invention also relates to a device.

This is characterized in that the device collects EEG signals from two or more electrodes and by signal analysis identifies pre-seizure characteristic changes in the EEG signal such as declining frequency content and increasing amplitude and after identification of the characteristic EEG changes delivers a warning signal.

The device thereby becomes simple, robust and highly portable.

Further preferred embodiments of the device are defined in claim 10.

The invention will now be explained more fully with reference to the drawings, in which.

Figure 1:
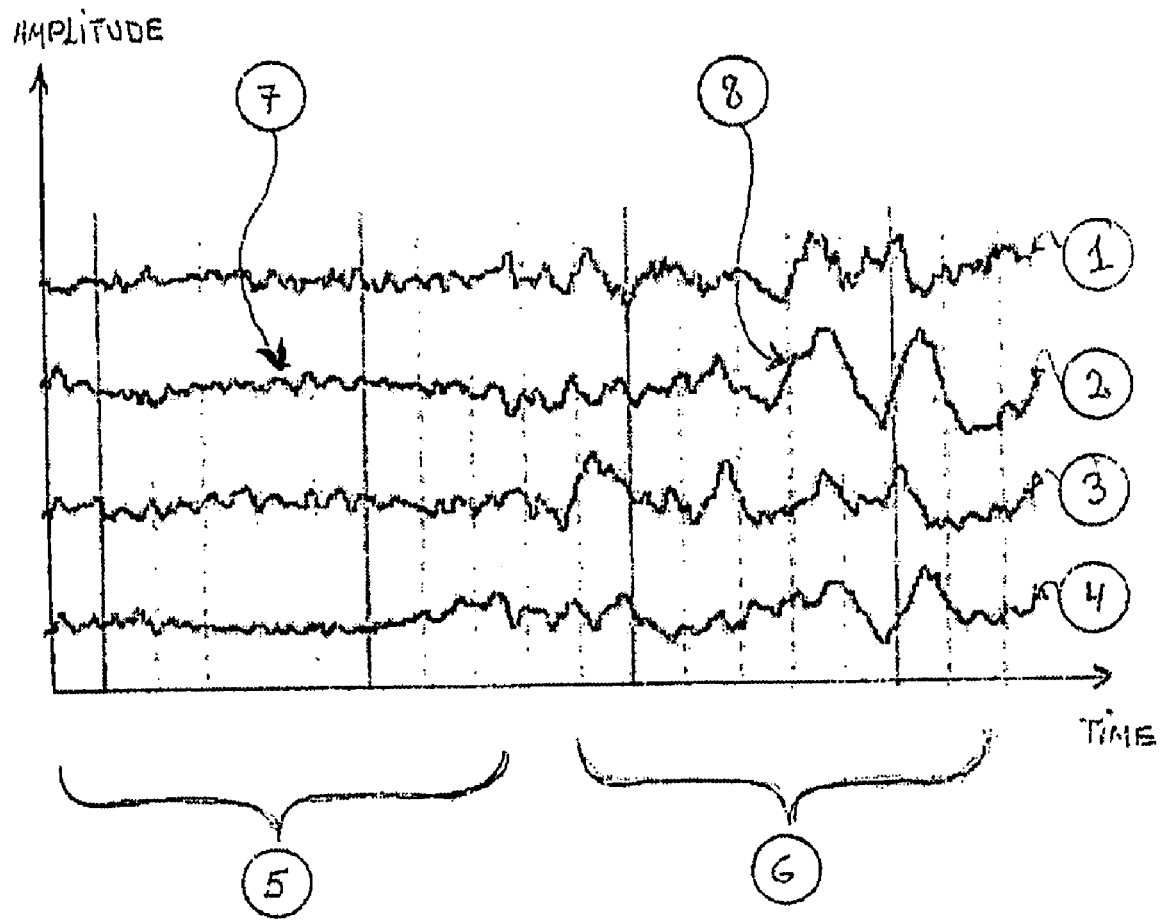
FIG. 1 shows an example of EEG signal sequences with both normal signals and the pre-seizure characteristic changes.

In FIG. 1 is shown part of four EEG signals derived from a person in advance of a hypoglycaemic attack. The four signals, which originate from different electrodes placed on the person's head skin, have been given the numbers 1 through 4.

The EEG signals are drawn in a co-ordinate system with indication of time on the horizontal axis and the signal amplitude on the vertical axis.

The time sequence specified with 5 shows a normal process of the EEG signals, while the time sequence specified with 6 shows the EEG signal in advance of a hypoglycaemic attack.

In the normal time phase 5 the EEG signals as shown with 7 are characterized in that they oscillate with a given mean frequency and with a given mean amplitude, which is comparable for all the four shown EEG signal derivations.

In the pre-seizure time phase 6 it is clearly seen, as indicated with 8, that the EEG signal in this phase is changed both significantly and characteristically. The wavelength of the signal becomes notably increased, similar to a comparable frequency reduction, concurrent with the signal amplitude being strongly increased.

The listed characteristic changes in the EEG signals in the pre-seizure phase often occurs several minutes before a hypoglycaemic attack is triggered. Hereby there is sufficient time to give an early warning to the person on the basis of the detected EEG signal changes. The person can then prevent the seizure, e.g. by consuming a sugary food product.

As it appears from FIG. 1 there are relatively notable changes in the EEG signal in the phase in advance of a hypoglycaemic attack. For the same reason it is relatively simple to detect these changes by the use of appropriate signal analysis algorithms.

The signal analysis can be performed in both the time- and frequency domain and can be based on more in other applications well-proven algorithms such as e.g. Baye's methods, logistic regression or neural networks. Tests have shown that algorithms based on Baye's methods, including bayesian classifier has been especially appropriate in order to, with high precision, detect the pre-seizure characteristic changes in the EEG signals.

It can be appropriate to build in dynamics in the signal processing algorithms in such a way that these are continuously adapted to the single person, who is going to be warned. Such a dynamic adaptation of the warning algorithms is a part of the present invention.

In order to achieve the best possible result of the signal processing it is appropriate to pre-filter the EEG signals including e.g. by band-pass filtering these, in order to eliminate noise from other signal sources in the highest possible extent.

Regarding signal analysis it is always aimed for to get the best possible signal/noise ratio. It will therefore be optimal to place the signal electrodes directly in the brain, from where the signal activity, which it is desired to measure, originates.

Tests have shown that recording of the blood sugar concentration occurs in the brain's hypothalamus area.

It is thus a part of the present invention to place electrodes directly in the hypothalamus area in order to achieve the best possible signal/noise ratio on signals for warning of hypoglycaemic attacks.

Figure 2:
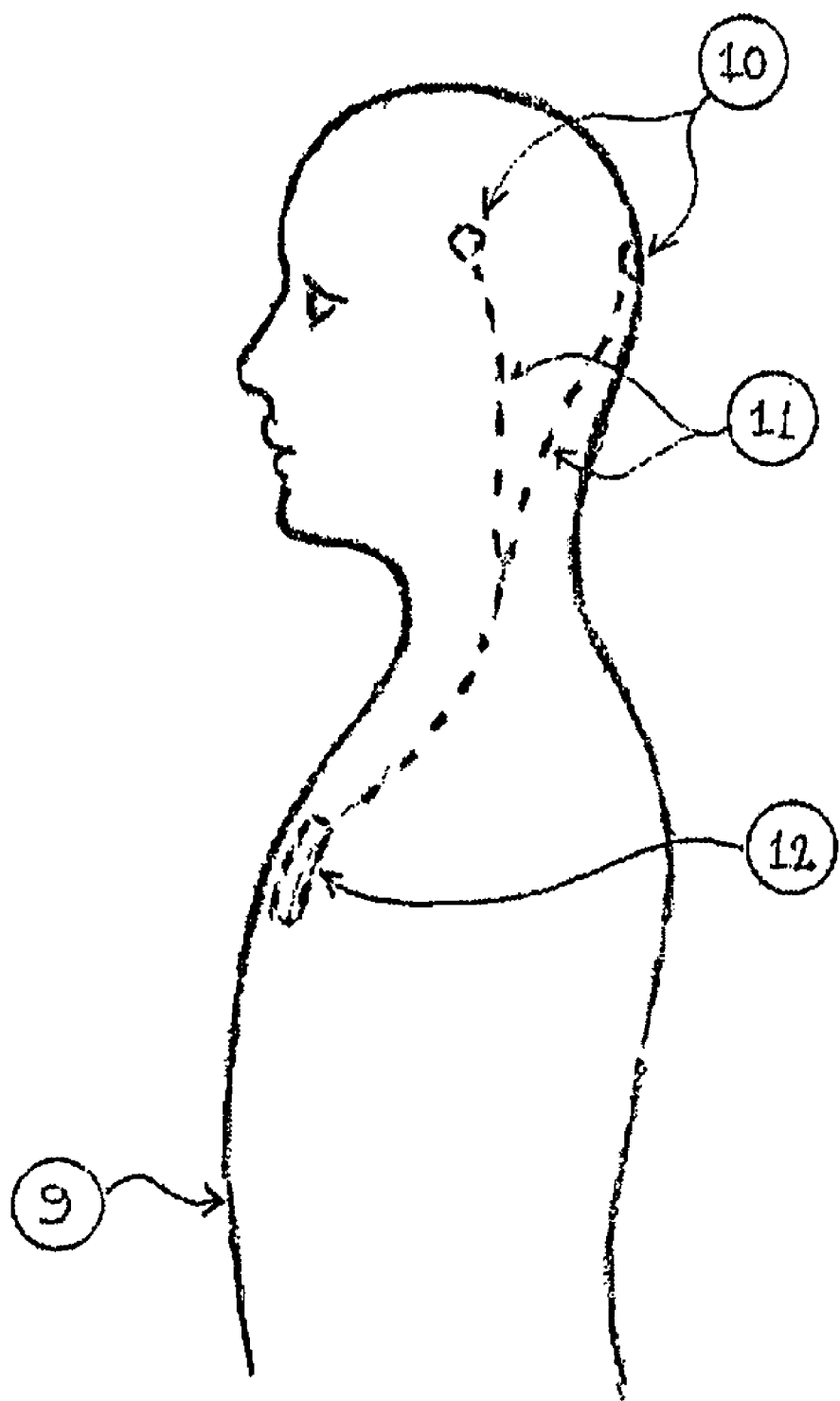
FIG. 2 shows a person with a subcutaneously placed hypoglycaemic seizure warning system.

FIG. 2 shows a person 9 provided with a warning system in accordance to the invention. Subcutaneously placed electrodes 10 record the EEG signals, which via wires 11, drawn under the skin, are lead to a signal processing unit 12, which is also placed below the skin.

The signal processing unit 12 processes via the implemented signal processing algorithms the measured EEG signals, and when the previously mentioned pre-seizure characteristic changes in the signals are detected, the unit 12 delivers a warning signal to the person 9.

The unit 12 is in FIG. 2 shown placed in the person's upper chest region, but can obviously also be placed a random place, e.g. behind the neck or where it seems the most appropriate for the single individual.

Figure 3:
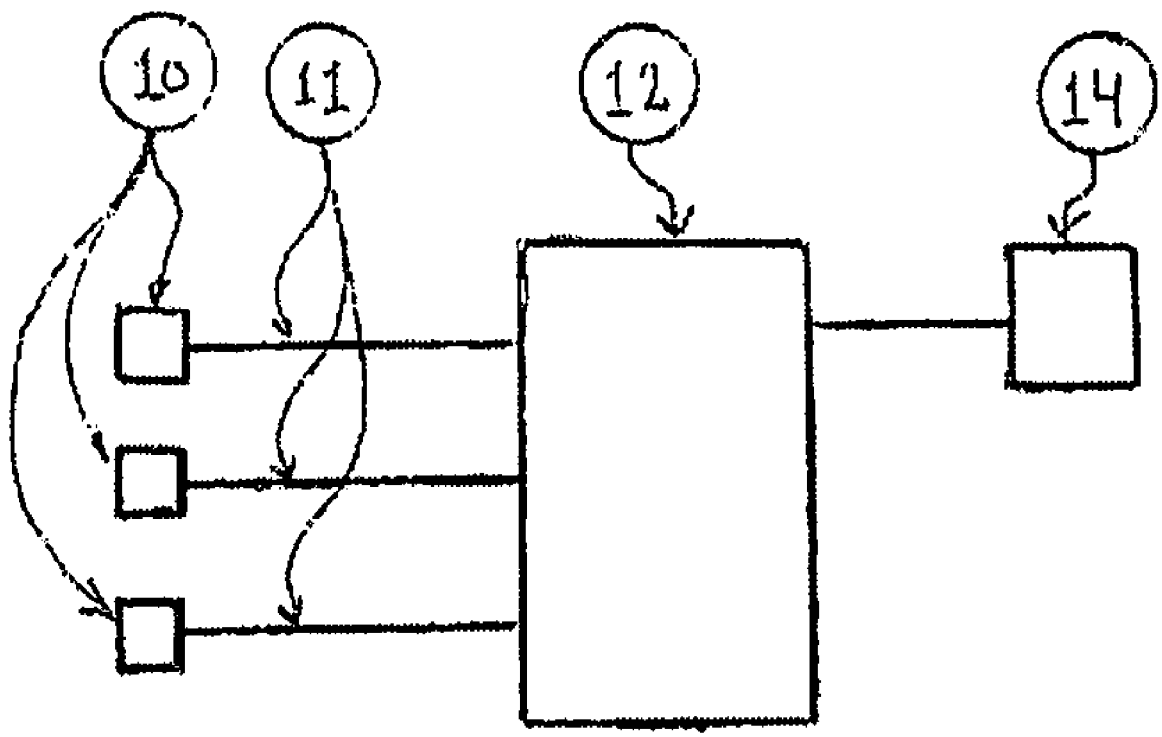
FIG. 3 shows a block diagram of the warning system from FIG. 2.

A block diagram for the system shown in FIG. 2 appears in FIG. 3.

Since the unit 12 is placed below the skin the alarm to the person can e.g. be delivered via a vibrator 14 integrated in the unit 12.

In FIG. 3 is shown 3 EEG electrodes from where the signals are lead to the signal processing unit 12. In practice any number of electrodes from two and more can be used, and the shown number is therefore not any limitation of the invention.

Even though the system in terms of signal is designed in order to achieve as high a signal/noise ratio as possible, there can probably arise situations where loud noise from the environment will reduce the possibility of sufficiently detecting the characteristic pre-seizure changes in the EEG signals.

In such a situation the system unit 12 can be programmed to deliver a warning signal to the person 9, which indicates that the seizure surveillance efficiency is lowered because of external noise. Such a warning signal, which must be separable from the normal pre-attack warning signal, can help the person, if possible, to remove or reduce the external noise source.

By differentiating the signal giver, e.g. by giving each signal a particular vibration frequency, several types of alarm- or information signals can be delivered, e.g. about the charging state of the energy supply.

The unit 12 must in order to function optimally be provided with electronics for adaptation of impedance for the electrodes and signal boosters and means for digitization of the analogue EEG signals. The digitized signals are subsequently processed in a calculation circuit such as a digital signal processor.

The unit 12 can be provided with a battery for energy supply.

The service life of the battery obviously depends of the choice of the electronic components, which are a part of the unit 12.

With present-day technique a service life of several years will be achievable. The service life and the size of the product will, however, to a certain extent always be proportional.

In those cases where e.g. the product's size is of decisive importance, it can be an advantage to split the system into a part, which is placed under the patient's skin and which only demands a minimum of power and an external part, which demands more power.

Figure 4:
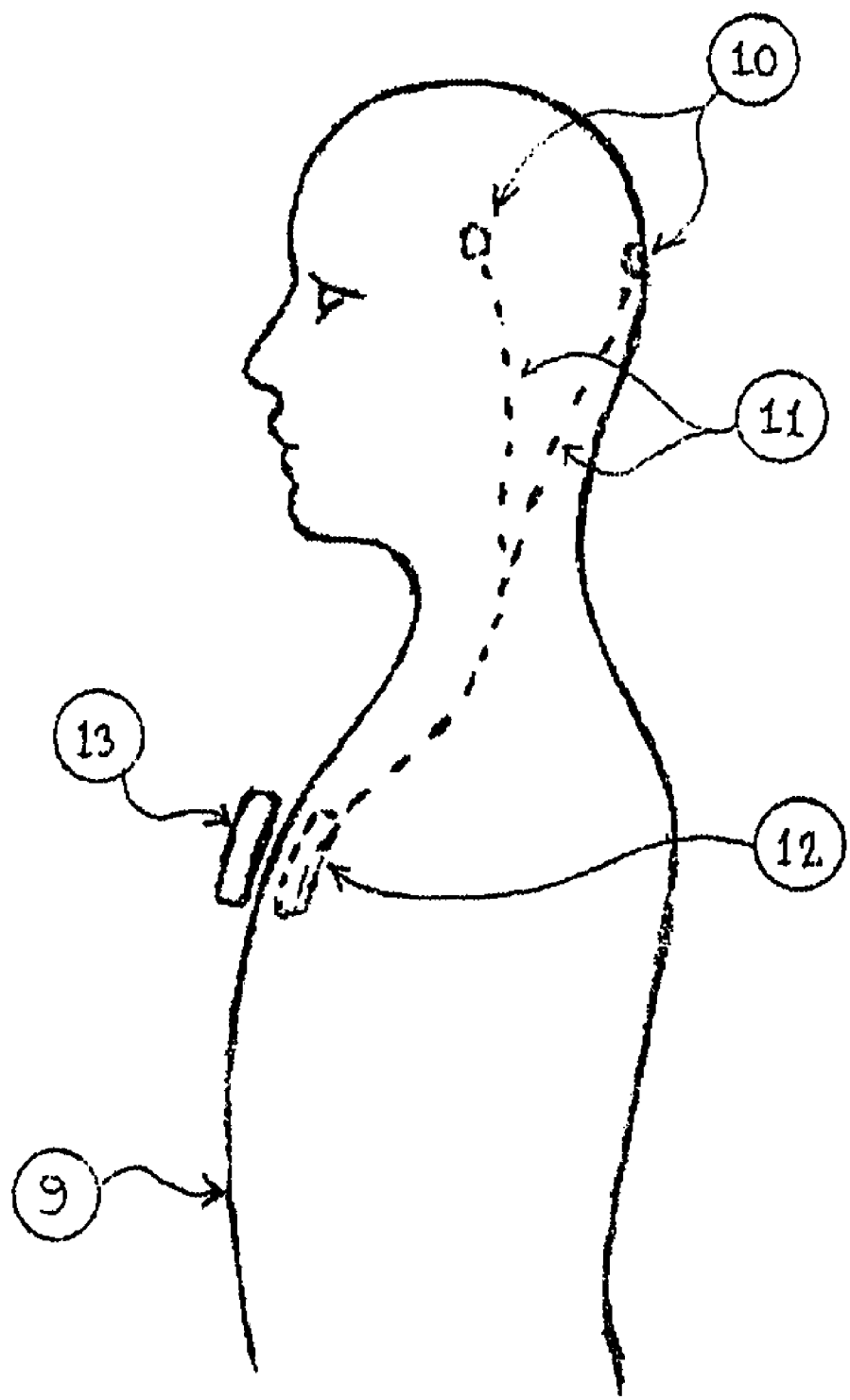
FIG. 4 shows a person with a warning system, which is partly subcutaneously placed and is partly external.

A warning system, which consists of an internally placed part below the patient's skin and an external part, is shown in FIG. 4.

In a system as shown in FIG. 4, the internal unit 12 can solely consist of an interface unit with a low power draw, which gathers the EEG signal from the electrodes and transmits them wirelessly through the skin to an external unit 13, which can e.g. be placed in the breast pocket of a shirt.

Figure 5:
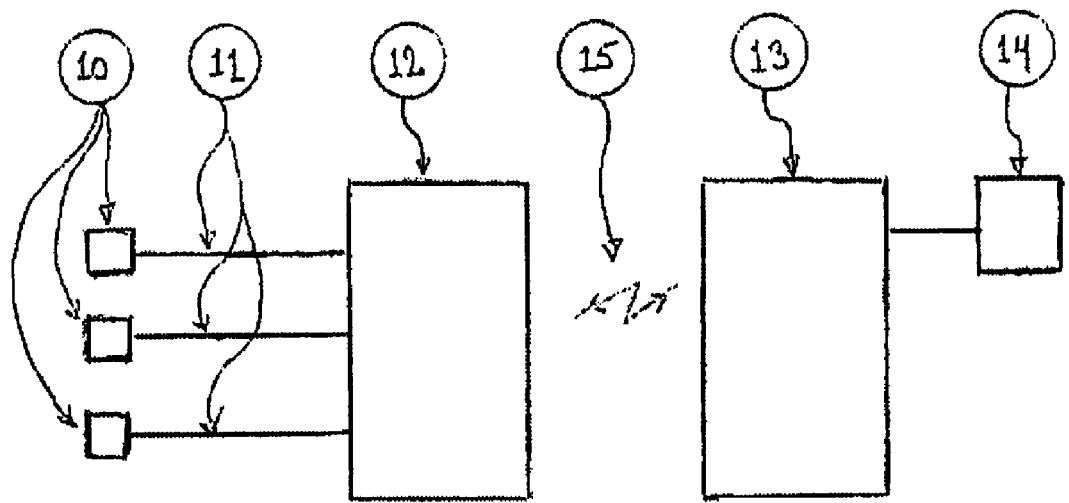
FIG. 5 shows a block diagram of the warning system shown in FIG. 4.

A block diagram of the system shown in FIG. 4 is seen in FIG. 5.

The unit 13 can in this example contain the more power demanding components, including the signal processing unit and the alarm signal giver 14, and electronics for wireless communication with the unit 12, which is placed under the skin.

When the signal giver is externally placed, the alarm, which is delivered from 14, can e.g. be an acoustic warning device as an alternative to a vibrator.

It is also possible to have a configuration like the one shown in FIG. 4, where the unit 12 is the complete unit with integrated signal processor and alarm giver, and where 13 in the principle is just a battery charging circuit, which wirelessly through the skin can charge the batteries in the unit 12. Such a battery charging can be produced on the basis of known techniques for wireless charging of batteries, e.g. through magnetic interaction of spools in respectively the charger/sender 13 and the receiver 12, which is going to be charged.

In case the unit 12 is provided with a signal processor, it will often be appropriate to provide the unit 12 with a communication circuit so that the signal processing program can wirelessly be updated from an external computer unit. With the application of a wireless communication circuit, it will at the same time be possible to transfer data from the unit 12 to the external unit 13 or one or more substituting external units in the form of data collection units or computers.

The present invention covers all combinations of system compositions, which directly or indirectly can be derived from the drawings 2 through 5 and the supplemental description to these.

The invention claimed is:

1. Method for warning of imminent hypoglycaemic attacks for people such as diabetics characterized in that the warning is based on analysis of one or more electroencephalographic (EEG) signals from a person without the use of electrocardiographic (ECG) signals, said method comprising:
   providing said person with a portable hypoglycaemic attack warning system comprising an interface unit implanted below the person's skin and an externally worn unit, said implanted interface unit having connected thereto implanted EEG signal gathering electrodes and further comprising a wireless signal transmitter, said externally worn unit comprising a signal processing unit for wirelessly receiving signals transmitted by the interface unit and for performing analysis of said signals for identifying characteristics therein indicative of an imminent hypoglycaemic attack; wirelessly receiving transmitted EEG signals in said signal processing unit and performing analysis of said signals therein so as to detect an imminent hypoglycaemic attack and
   giving a warning to said person that a said attack is determined to be imminent.

2. Method for warning of hypoglycaemic attacks according to claim 1 characterized in that the warning is given after signal analytic identification of pre-seizure characteristic EEG changes which include at least one of decrease in frequency and increase in amplitude.

3. Method for warning of hypoglycaemic attacks according to claim 1 characterized in that the EEG signals are registered from two or more said electrodes placed intracranially or subcutaneously.

4. Method for warning of hypoglycaemic attacks according to claim 3 characterized in that that the EEG signals from the electrodes are transmitted via subcutaneously drawn wires to a subcutaneous placed said signal interface unit.

5. Method for warning of hypoglycaemic attacks according to claim 1 characterized in that the EEG signals in advance of the signal analysis are filtered through band-pass filtering.

6. Method for warning of hypoglycaemic attacks according to claim 1 characterized in that the signal analysis of the EEG signal is carried out in the time- or frequency domain.

7. Method for warning of hypoglycaemic attacks according to claim 1 characterized in that the pre-seizure characteristic EEG signal changes are detected by application of signal analysis based on algorithms such as Baye's methods including bayesian classifier, logistic regression or neutral network.

8. A method as claimed in claim 7, wherein the pre-seizure characteristic EEG signal changes are detected by application of signal analysis based on an algorithm which is continuously adapted to the person.

9. A hypoglycaemic attack warning device for warning of imminent hypoglycaemic attacks for people such as diabetics comprising an interface unit to be implanted below a person's skin and an externally worn unit, said interface unit having connected thereto electroencephalographic (EEG) signals gathering electrodes suitable for implantation in the body of the person person and further comprising a wireless signal transmitter, said externally worn unit comprising a signal processing unit for wirelessly receiving signals transmitted by the interface unit and for performing analysis of said signals without using electrocardiographic (ECG) signals for identifying characteristics therein indicative of an imminent hypoglycaemic attack and further comprising means for giving a warning to said person when a said attack is determined to be imminent.

10. Method for warning a person of imminent hypoglycaemic attacks characterized in that the warning is based on analysis of one or more electroencephalographic (EEG) signals from the person without the use of electrocardiographic (ECG) signals, said method comprising:
    providing said person with a portable hypoglycaemic attack warning system comprising an interface unit implanted below the person's skin and an externally worn unit, said implanted interface unit having connected thereto implanted electrodes for gathering EEG signals, said externally worn unit comprising a signal processing unit for wirelessly receiving said EEG signals;
    wirelessly receiving said EEG signals in said signal processing unit and performing analysis of said signals therein so as to detect an imminent hypoglycaemic attack; and
    providing a warning to said person that said attack is determined to be imminent.

* * * * *